(12) United States Patent
Dorronsoro Díaz et al.

(10) Patent No.: US 8,876,289 B2
(45) Date of Patent: Nov. 4, 2014

(54) INSTRUMENT FOR SIMULATING MULTIFOCAL OPHTHALMIC CORRECTIONS

(75) Inventors: Carlos Dorronsoro Díaz, Madrid (ES); Susana Marcos Celestino, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 233 days.

(21) Appl. No.: 13/267,123

(22) Filed: Oct. 6, 2011

(65) Prior Publication Data

US 2012/0075585 A1    Mar. 29, 2012

Related U.S. Application Data

(63) Continuation of application No. PCT/ES2010/070218, filed on Apr. 7, 2010.

(30) Foreign Application Priority Data

Apr. 8, 2009  (ES) .................................. 200930055

(51) Int. Cl.
| | | |
|---|---|---|
| *A61B 3/024* | (2006.01) | |
| *A61B 3/08* | (2006.01) | |
| *A61B 3/10* | (2006.01) | |
| *A61B 3/028* | (2006.01) | |

(52) U.S. Cl.
CPC ... *A61B 3/10* (2013.01); *A61B 3/08* (2013.01); *A61B 3/024* (2013.01); *A61B 3/0285* (2013.01); *A61B 3/028* (2013.01)
USPC ........... 351/201; 351/202; 351/203; 351/206; 351/216; 351/246; 351/221; 351/222

(58) Field of Classification Search
CPC ............ A61B 3/00; A61B 3/02; A61B 3/028; A61B 3/0285; A61B 3/024
USPC .................. 351/216, 246, 200–206, 221–222
See application file for complete search history.

(56) References Cited

U.S. PATENT DOCUMENTS

| | | | |
|---|---|---|---|
| 5,208,619 A | | 5/1993 | Campbell |
| 7,070,276 B2 | * | 7/2006 | Koretz .......................... 351/206 |

(Continued)

FOREIGN PATENT DOCUMENTS

| | | | |
|---|---|---|---|
| EP | PCT/EP2005/009354 | * | 3/2006 |
| WO | 01/89372 | | 11/2001 |

(Continued)

OTHER PUBLICATIONS

International Search Report issued Jul. 26, 2010 in International (PCT) Application No. PCT/ES2010/070218.

*Primary Examiner* — Scott J Sugarman
*Assistant Examiner* — Daniele Manikeu
(74) *Attorney, Agent, or Firm* — Wenderoth, Lind & Ponack, LLP.

(57) ABSTRACT

The invention relates to an instrument for simulation of multifocal ophthalmic corrections, comprising two optical channels with different optical power values in the beams coming from the object observed, wherein at least one channel comprises a Badal system. This instrument simultaneously provides images of objects near and far focused. The system provides the same optical magnifications for each channel, regardless of the optical power thereof, and produces superimposed retinal images with different degrees of focus which, unlike other devices, are all of the same size. The instrument allows simulating different optical powers for near vision and different refractive corrections for distant vision.

8 Claims, 2 Drawing Sheets

(56) References Cited

U.S. PATENT DOCUMENTS

| | | | |
|---|---|---|---|
| 7,131,727 | B2 | 11/2006 | Jones et al. |
| 7,455,403 | B2 | 11/2008 | Jones et al. |
| 2007/0139614 | A1 | 6/2007 | Lindacher |
| 2009/0009715 | A1* | 1/2009 | Mensink ................ 351/213 |
| 2009/0009716 | A1* | 1/2009 | Gorschboth et al. ......... 351/221 |
| 2011/0109877 | A1* | 5/2011 | Pujol Ramo et al. ........ 351/206 |

FOREIGN PATENT DOCUMENTS

| | | |
|---|---|---|
| WO | 2005/004705 | 1/2005 |
| WO | 2008/083015 | 7/2008 |
| WO | 2009/017516 | 2/2009 |
| WO | 2009/017987 | 2/2009 |

* cited by examiner

INSTRUMENT FOR SIMULATING MULTIFOCAL OPHTHALMIC CORRECTIONS

This application is a Continuation of International Application No. PCT/ES2010/070218, filed Apr. 7, 2010, which is hereby incorporated by reference in its entirety.

The present invention generally relates to the field of ophthalmology, and in particular to the field of ophthalmic corrections for presbyopia.

STATE OF THE ART

The main optical components of the human eye are the cornea, which acts as a static element and provides most of the power of the eye, and the lens, which acts as a dynamic focusing system changing its power (relatively lower). This focusing ability of the human eye, and in particular of the lens, so-called accommodation, is lost with age. The most immediate solution is to use lenses for different distances, typically two, near and far. But this solution is only viable for glasses, not for contact or intraocular lenses.

Another common solution is to use simultaneous vision systems that provide on the retina, at the same time, images corresponding to the vision at different distances. Typically, the image obtained with regions of the lens focused at near distance and the image obtained with regions of the lens focused at far distance are superimposed on the retina. A superimposed far/near image will be projected on the retina regardless of the distance at which the patient is looking at. Therefore, if a nearby object is observed, this will appear focused on one of the superimposed images, and unfocused on the other, and similarly, if a distant object is observed.

A different approach usually implemented in glasses, is to use alternating ("multifocal") vision systems, in which, by changing the line of sight, the eye can switch between near and distant vision areas that do not mix, and each of them is larger than the pupil (as opposed to simultaneous vision systems, wherein each refractive area is smaller than the pupil). Simultaneous vision is the most common option in contact and intraocular lenses for correcting presbyopia. In fact, most of the designs of multifocal contact and intraocular lenses are based, in one way or another, on simultaneous vision systems (see for example patent applications WO/2009/017987 and WO/2009/017516).

Normally simultaneous vision is based on the availability of concentric zones of different refractive power on the lens. The relative weight of each area provides the relative weight of each image (near, distant, and intermediates) superimposed on the retina. Progressive multifocal lenses (aspheric) can be considered an extreme simultaneous vision system, on which a continuum of images, corresponding to intermediate distances, is superimposed. As a result of the design of the lens, the multifocality is obtained at the expense of a loss of contrast in the images, which is usually well tolerated by patients since, rather than a blurred image, the projected image consists of a sharp image superimposed on a diffuse background. In short, a general loss of contrast without loss of resolution is usually well tolerated by the human visual system.

Generally, in the optometry practice, a trial and error procedure is followed to identify the most suitable simultaneous vision contact lenses. Normally, different lenses are tried until the patient adapts to one. However there are patients who do not tolerate well any lens design. The process to identify those patients takes several weeks during which they pay multiple visits to the contactology office and will have used several pairs of lenses. Obviously, with intraocular lenses, this trial and error process is not feasible; therefore, patients implanted with simultaneous vision intraocular lenses who are not able to adapt to them either need to live with a suboptimal correction or have it explanted.

To improve this situation, the identification of patients who do not tolerate or get adapted to a simultaneous vision correction must be ideally performed by providing them with a temporary and non-invasive visual experience of simultaneous vision, so that their response, compliance, adaptation degree, satisfaction level, etc. can be documented, as a previous step to the selection of other parameters (correction, addition, type of design, pupils, type of setting).

The phoropter is an instrument commonly used to provide a patient with the visual experience corresponding to a different refractive status (nearsightedness, farsightedness and astigmatism), and to evaluate the patient's visual acuity in the identification of letters at near and far distances. Phoropters work by simply placing different lenses in front of the eye. They provide the ability to simulate various distances (by observing far or near objects), but not in a simultaneous manner. Moreover, the different power lenses used by the phoropter produce retinal images of different sizes; unlike (to a large extent) in contact lenses and in intraocular lenses.

Badal systems, widely used in visual optics and in particular in the study of accommodation and presbyopia, can be applied to solve this problem, since these are optical systems that induce convergence (different degrees of myopia or hyperopia) without changing the magnification. In other words, these simulate different distances from the observed object, without changing its position and size. There are several Badal system configurations, but generally they are based on the optical projection of the eye pupil plane on another plane outside the eye, usually with unit magnification, using two optical elements (lenses or mirrors), one of which is placed at a focal distance from the eye pupil, and the other at a focal distance from the projected pupil, such that the relative motion of some elements with respect to others induces a convergence proportional to the traveled distance. By using a conventional Badal system the simulation of the observation at various convergences can be achieved, with retinal images of the same size. However, the superposition of both images, like in simultaneous vision, is not achieved. Badal systems have been previously used as constituent elements for refractometers, keratometers and systems for measuring the optical power of lenses (U.S. Pat. No. 5,208,619).

An alternative approach for producing simultaneous visual experience is by the projection of digital images simulated on a screen, offering the patient a simulation of what would be the retinal image provided by the multifocal element. This procedure is commonly used in research laboratories, but its application is generally limited to controlled laboratory conditions. In addition, the combination of the optical degradation of each eye with the lens can not be correctly simulated, as the patient's eye optics would additionally affect the image quality. In addition, the optical quality is highly dependent on the diameter of the eye pupil.

The use of adaptive optics systems greatly improves the quality of the simulation, since it is performed in an optical environment, and not on the computer. However they require very expensive and complex equipments, generally limited to laboratory environments, and usually unable to emulate abrupt transitions and large additions. Phase masks, a relatively inexpensive solution for the simulation in the optical environment, can be subject to centration problems in their projection onto the eye, and their design can not be altered to simulate different conditions.

Jones and Buch (U.S. Pat. Nos. 7,131,727 and 7,455,403) proposed a purely optical approach based on lenses, prisms and polarizers that seek to emulate simultaneous vision providing the eye with two optical channels, each of which has a different power. The system has a receptacle on one of the channels in which different power lenses can be inserted, and a common receptacle for adding power to both channels at once.

This system has several drawbacks. First, the coupling between the lenses and the eye is not optimal, whereby the effective power of the lenses is very different from its nominal value. In addition, each channel has different magnifications, wherewith the retinal images formed through each one have different sizes and therefore the resulting superposition differs from that obtained with a simultaneous vision contact lens or intraocular lens.

The present invention provides an instrument for simulating multifocal ophthalmic corrections that meets the described needs overcoming the drawbacks of previous systems.

DESCRIPTION OF THE INVENTION

General Description of the Invention

FIG. 1 shows a simple scheme of the operation of the invention, based on a purely optical system that includes only mirrors, beam splitters and lenses with spherical surfaces, without needing software for computation or processing images, nor display elements, active or aspheric optical elements, providing compactness, simplicity and low cost thereto. The instrument comprises two observation channels, one corresponding to distant vision and another for near vision, providing the eye different vergences (optical power). In the scheme, the upper channel induces "n" diopters and the lower one "m" diopters. As in the invention described in U.S. Pat. Nos. 7,131,727 and 7,455,403, one of the keys for the proper operation of the present invention is that the eye is able to simultaneously observe objects by both optical channels, and that the optical axes at the output channel match exactly, such that two perfectly superimposed and simultaneous images are produced on the retina. Only the focusing status of one image relative to the other must be changed between images, as occurs in simultaneous vision multifocal corrective lenses.

To avoid the inconvenience of occurring different optical magnifications resulting in images on the retina with slightly different sizes, caused by the use of different lenses or curve mirrors in each channel, the present invention comprises the use of Badal systems in at least one of the channels for inducing the vergence. This allows providing the same optical magnification, whatever the vergence, with the result of superimposed retinal images of different focusing degree and the same size, which is one of the main differences of the present invention over the state of the art.

By providing simultaneous vision by means of retinal images having the same size through two optical channels of different vergence, the simulation is free of artifacts. Thus, the instrument can be used to test pure bifocality, thus eliminating additional problems related to centration, pupil size, folding or conformity that naturally occur in real lenses, and which degrade the image quality and distort the actual willingness of the patient to simultaneous vision. The system is versatile because it allows simulating different additions for near vision, and different refractive corrections for distant vision.

Besides its low cost and simplicity, systems of very small size and weight can be achieved, to obtain portable systems that can be used like a telescope or like binoculars. This allows a natural observation of the environment, and performing tasks such as short distance reading, middle distance observation (working on the computer, searching in a library, etc.) or the evaluation of long-distance observation (traffic signals, signs, etc. . . . ).

An alternative use of the present invention is its use as a training instrument for simultaneous vision, since the image through this device will be cleaner than that of the final system wherein other effects as pupil size, conformity, folding, decentrations, tilts, and so on are added.

Another possible use of the present invention is to support the explanation by the surgeon or the eye care professional about the types of lenses to be used, for taking informed decisions by the patient or training on their use.

DETAILED DESCRIPTION OF THE INVENTION

The invention consists of an instrument for simulating multifocal ophthalmic corrections characterized by comprising two optical channels and which provide the pupil with two simultaneous coaxial beams from the observed object. At least one of the channels travels through a Badal system, which introduces a different vergence (in the terminology of the multifocality, it is said that the Badal system introduces an addition). The upper channel induces "n" diopters and the lower one "m" diopters. For a subject without refractive errors, a desirable configuration would be n=0 for distant vision and m between 0 and 3 for near vision, depending on the level of presbyopia and the needs of the patient. Following the nature of the accommodation, it is normal to keep the distant vision channel stable while the near vision channel can be adjustable to test different additions. Therefore, it is desirable, if there is only one variable addition Badal system, to be in the near vision channel.

It is an essential condition for the proper operation of the embodiment of the invention that the optical axes of both output channels and thus the position of the retinal images, to match exactly as shown in FIG. 1. The recombination of both channels into one output channel towards the eye is achieved using an output beam splitter (DH1), which can be a semi-mirrored mirror, a coplanar plate, a prism or a similar optical element. The correct adjustment of the tilt of DH1 is critical, as it is the optical element controlling the alignment of the optical axes of both channels.

During the observation of near or three-dimensional objects parallax problems can occur if the input optical axes (from the observed object to the system) do not coincide, as in the case of FIG. 1. It is therefore recommended, although not essential, to produce coincident input axes, by placing an input beam splitter (DH2) for channeling the beam coming from the observed object to one or another channel. FIG. 2 shows a scheme illustrating one of the several possible solutions to combine both the input and output optical axes.

The beam splitters used control the amount of light passing through each channel, just like the proportion of the areas of different refraction on a multifocal lens governs the relative weight in the image of the near and distant vision. By selecting the beam splitters, different types of simultaneous vision multifocal lenses can be simulated, and in particular, different balances between distant and near vision (typical examples are 30/70, 50/50 or 70/30). The same can be done by means of filters of neutral density placed in one of the channels, although this t entails higher losses of the light energy coming from the object.

The correction of the refractive errors that the patient may have can be performed by other ophthalmic corrections (the patient's own glasses or contact lenses, or a phoropter), although an alternative solution is to have two sets of Badal systems, one in each channel. In this case one will correct distant vision by introducing the necessary convergence, and the other will provide an extra addition to simulate bifocality by simultaneous vision.

An additional argument for using a Badal system in each channel is that, although strictly speaking the use of a Badal system does not change the magnification by changing the convergence, introducing a Badal system in a channel represents a change in the effective distance to the object. In fact, the Badal system projects the pupil of the eye to a different plane, located between the eye and the observed object. That plane defines the actual distance to the object, and therefore the optical magnification and the scale (size of the retinal images). If the Badal system is used only in one of the channels, the effective distances to nearby objects through both channels would be unbalanced, which could produce significant scale changes when the actual distance to the observed object is small. The simplest mechanism to compensate near distances is to use two Badal systems, one in each channel, although one of them can be fixed. FIG. 3 shows a scheme illustrating one of the possible configurations. The compensation of the distance balance by means of another Badal system involves a change in configuration and the introduction of additional mirrors (E1 and E2), but no further losses.

The above description represents simultaneous vision bifocality. However it can be extended to the simulation of simultaneous vision multifocality, adding a channel with a Badal system for each intermediate position between near and distant vision. It should be taken into account that the number of channels can not be indefinitely increased, since each of them introduces losses in the light energy coming from the object.

The potential uses for instrument are broad, including the identification of presbyopic patients (with presbyopia) who suitable (or not) for simultaneous vision multifocal ophthalmic corrections. Direct observation through the system can provide the first data. Some patients will not tolerate the loss of contrast or the new structure of the retinal images, rejecting the simultaneous vision experience even in this preliminary evaluation phase. A more complete assessment can be made by measuring the distant and near visual acuity through the system, which can identify potential degradation of visual function with simultaneous vision corrections, since these losses will eventually cause the rejection of the solution.

An alternative use of the present invention is to sustain patient education and provide support to the explanations of the eye care professional or ophthalmologist on simultaneous vision, which will favor the informed decision making on the ophthalmic correction to be adopted. The patient may use the system for previous, non-invasive, training of the simultaneous visual experience. For comparison with the best possible bifocal correction, and to illustrate the degradation introduced by the simultaneous vision, the channels of the system can be presented to the observer alternating in time, and not simultaneously. This can be achieved by replacing the beam splitters by fast repositioning mirrors.

The system can be used in researching, designing and testing new multifocal ophthalmic corrections.

At least P1 is movable on the axis indicated by the arrow with two points, so that its greater or lesser distance from the axis formed by the lenses L11 and L12 determines the addition in the near vision channel. R1 represents a ruler to mark the addition imposed (in diopters).

EMBODIMENT OF THE INVENTION

Figure 4:
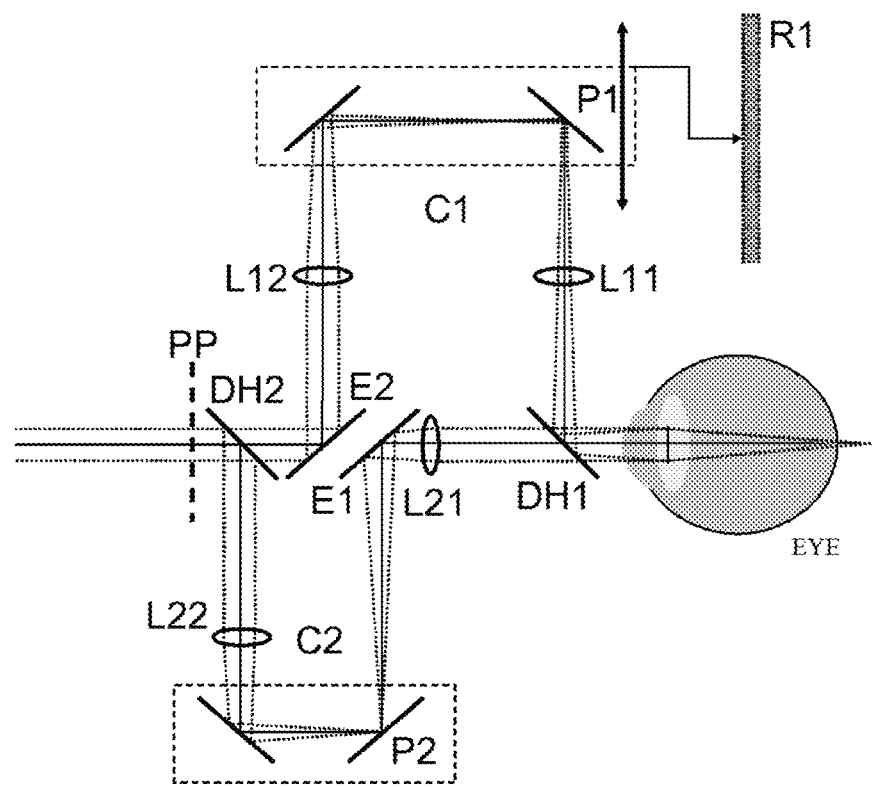
FIG. 4. Scheme of the instrument described in the invention in a configuration with two optical channels with coincident axes and wherein both channels include a Badal system, corresponding to a particular embodiment of the scheme described in FIG. 3. The elements DH1, DH2, E1 and E2 are the same as described in FIG. 3. The dashed rectangles represent the near (C1) and distant (C2) vision channels. P1 and P2 are platforms, with mirrors (internal lines, oblique to the rectangles that represent the channels) placed at an angle of 90° to each other, and which form part of the Badal system for the near and distant vision channels, respectively. The lenses of the Badal system are represented as ellipses: L11 and L12 for the lenses of the near vision channel (C1) and L21 and L22 for the lenses of the Badal system for the distant vision channel (C2). The Badal system of the near vision channel (C1) projects the eye pupil onto the plane indicated by the dashed line PP.

As a practical embodiment of the invention without limiting thereof, described below is an optical instrument that implements in a simple way the main concepts object of this invention. FIG. 4 shows the main elements of said instrument.

Figure 1:
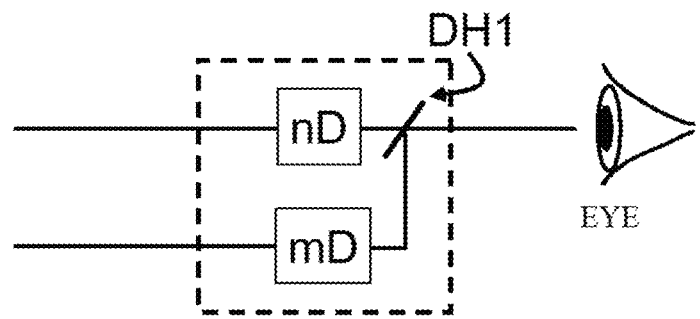
FIG. 1. Scheme of the instrument described in the invention in its simplest configuration (two optical channels). Two channels are shown with superimposed signs to indicate the channel for distant vision, which corrects "n" diopters (nD) of refractive error of the subject and the channel for near vision, which introduces an addition (optical power difference) of "m" diopters (mD), by using a Badal system. The optical beams corresponding to the channels are re-combined into a single one, which is collected by the eye, using an output beam splitter (DH1).
Figure 2:
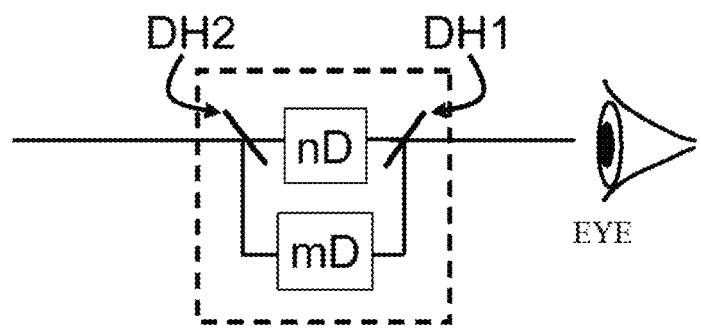
FIG. 2. Scheme of the instrument described in the invention in a configuration with two optical channels with coincident axes. The incoming beam is split into two beams by an input beam splitter (DH2), producing two channels nD and mD, equal to those described for FIG. 1 (and, therefore, at least one of them comprises a Badal system). The optical beams corresponding to the channels are re-combined into a single one, which is collected by the eye, using an output beam splitter (DH1).
Figure 3:
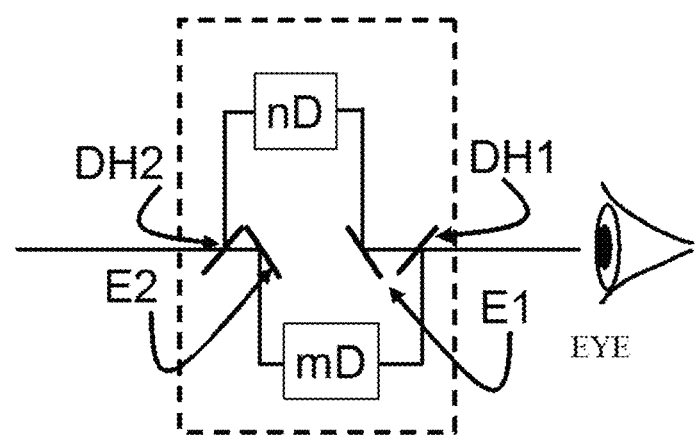
FIG. 3. Scheme of the instrument described in the invention in a configuration with two optical channels with coincident axes and wherein both channels comprise Badal systems. The effective distance to the nearest object in both channels is compensated in order to avoid scale changes by introducing the mirrors E1 and E2. The elements nD, mD, DH1 and DH2 designated are the same as those described in FIG. 2.

A beam splitter (DH1) is placed immediately before the eye, for redirecting its observation through two different optical channels. This example develops the system of FIG. 3 in which Badal systems are included on both channels, C1 and C2. The lens L11 (Badal lens of channel C1) is placed at a distance from the eye that roughly coincides with its nominal focal length. Behind it, two mirrors mounted on a platform P1, which is in turn mounted on a sliding rail. The degree of displacement, which can be manual or motorized and remotely controlled, is measured by means of a distance ruler R1, which can be any type of position sensor. Another lens L12 is positioned behind the two mirrors, which must have the same focal length than L11 so that the channel C1 has unit magnification, and which should be placed at a distance such that the optical path traveled from L11 be equal to the sum of L11 and L12 when the platform P1 is in the zero position of the ruler R1. When the platform slides towards the lenses, the optical path is shortened and the beam convergence simulates a nearby object, or what is the same, C1 simulates several diopters of addition. The level of diopter addition can be obtained from the reading of the ruler R1.

The focal length chosen for the Badal lens L11 establishes the total optical path of channel C1. In addition, it affects the accuracy of the ruler R1 and imposes a restriction on the maximum travel of the sliding rail, which limits the maximum addition that can be achieved. As a guide, a focal length of 50 mm represents a good compromise between the total size of the system, the precision in controlling the induced addition and the maximum achievable addition.

The Badal system (consisting of lenses L11 and L12 plus the mirrors of the platform P1) projects the pupil of the eye on the pupil plane PP (i.e., at a distance of one focal length of the lens L12, after having been reflected on E2) regardless of the position of platform P1. The distance from PP to the object, and not the distance from the eye to the object, defines the size of the retinal image.

To use the system at nearby distances from the object, a distant vision channel C2 is introduced. This channel C" is a replica, in terms of its optical elements, of the channel C1 (with the mirrors L21 and L22 of the same focal length that L11 and L12). However, the position of the platform P2 can be fixed at the position corresponding to zero diopters of addition, therefore abstaining from the sliding rail and the ruler. The arrangement of the elements in channel C2 is different from that of channel C1. They can not be exactly the same as then the different optical elements (beam splitters) would be superimposed in the space. There are, however, a multitude of different solutions of which the one shown in FIG. 4 is just one example. This channel also projects the eye pupil on plane PP which ensures that the optical magnifications and scales on the retina are exactly the same in both channels.

An alternative to the previous assembly, useful to compensate the refraction at far is to mount platform P2 on a sliding rail, and a ruler similar to R1. In that case, after compensating the distant vision with one of the channels, the other channel must be readjusted to provide the desired addition.

Another alternative to compensate the distant refraction in the system described in FIG. 4 is to place trial lenses on plane PP (or even a phoropter). This solution is conceptually different from that adopted in other inventions, as the trial lens is projected by the Badal system to the plane of the eye pupil, which is a proper optical coupling between the test lens (or the phoropter) and the eye. From the optical point of view, the lens is considered to be placed "inside" the eye, which causes no optical magnifications or scale changes in the retina, nor limits the field of vision. The compensation for near vision in this way would not affect the addition provided by channel C1. Due to the proper optical coupling of this invention, any type of optical observation system can be placed in plane PP of this system, such as an eyepiece (which would become bifocal) for any use (as examples, binoculars or microscopes).

Plane PP can also be used to place artificial pupils (typically circular apertures) wherewith the simultaneous vision is simulated at different pupil sizes.

The invention claimed is:

1. An instrument for a simulation of ophthalmic multifocal corrections for a generation of superimposed images, the instrument comprising:
    two optical channels, each of the two optical channels projecting a same observed object with a same magnification but different vergence, thus producing two projected images, such that each of the two projected images is projected through a corresponding optical channel of the two optical channels, and such that the two projected images are projected with a same size but different focusing status;
    a Badal system placed in one channel of said two optical channels for adding a vergence only to a light beam that passes through said one channel without changing the magnification; and
    an output beam splitter which recombines two light beams in a single light beam so that the two projected images of the same size and different focusing status are simultaneously superimposed forming a single multifocal image.

2. The instrument of claim 1, wherein the instrument further comprises another Badal system placed in another optical channel for adding a vergence only to a light beam that passes through the other optical channel without changing the magnification.

3. The instrument of claim 1, wherein the instrument further comprises an input beam splitter which generates two input light beams from a single input light beam.

4. The instrument of claim 2, wherein the instrument further comprises an input beam splitter which generates two input light beams from a single input light beam.

5. The instrument of claim 4, wherein the instrument further comprises two mirrors, one mirror per optical channel, placed between the input beam splitter and the output beam splitter.

6. An instrument for a simulation of ophthalmic multifocal corrections for a generation of superimposed images, the instrument comprising:
    two optical channels, each of the two optical channels projecting a same observed object with a same magnification but a different vergence, thus producing two projected images, such that each of the two projected images is projected through a corresponding optical channel of the two optical channels, and such that the two projected images are projected with a same size but different focusing status;
    an input beam splitter which generates, from a single input beam from the observed object, two input light beams that pass through the two optical channels;
    one Badal system per each of said optical channels for adding a vergence only to a corresponding input light beam maintaining a same size of the projected images in both optical channels but inducing a different focusing status;
    an output beam splitter which recombines two light beams in a single light beam so that the two projected images of the same size and the different focusing status are simultaneously superimposed forming a single multifocal image;
    two mirrors, one mirror per optical channel, placed between the input beam splitter and the output beam splitter; and
    two platforms, one per optical channel, each platform comprising two platform mirrors in an arrangement of an angle of 90° therebetween, one platform being placed between the input beam splitter and one of the two mirrors, and another platform being placed between the output beam splitter and another mirror of the two mirrors,
    wherein each Badal system comprises two lenses and the two platform mirrors of one of the platforms, such that one lens of one Badal system is placed between the input beam splitter and the one platform, and another lens of the same Badal system is placed between one platform mirror and the output beam splitter, wherein the two lenses of another Badal system are arranged so that one lens of the other Badal system is placed between the other mirror and the other platform, and another lens of the other Badal system is placed between the other platform and the output beam splitter, and wherein, at least one platform is mobile for changing the vergence added by the corresponding Badal system.

7. The instrument of claim 6, wherein the instrument further comprises a sliding rail on which the mobile platform is mounted, and a position sensor for measuring a movement of the mobile platform.

8. A method for a simulation of ophthalmic multifocal corrections for a generation of superimposed images, the method comprising:

generating, by means of a input beam splitter, two input light beams which project an observed object with same magnifications but with different vergences, thus producing two projected images of a same size but different focusing status;

adding, by means of a Badal system, a vergence to at least one of the two input light beams for changing the focusing status of a corresponding projected image without changing the size of the corresponding projected image; and recombining, by means of an output beam splitter, the two input light beams in a single light beam so that the two projected images of the same size and different focusing status are simultaneously superimposed forming a single multifocal image.

* * * * *